United States Patent [19]

Ishikawa

[11] 4,306,973

[45] Dec. 22, 1981

[54] MEDICAL LIQUID DISPENSER WITH FILTER MEANS

[76] Inventor: Soji Ishikawa, No. 6-22, 6-chome, Miyazaki, Takatsu-ku, Kawasaki City, Kanagawa Prefecture, Japan

[21] Appl. No.: 50,618

[22] Filed: Jun. 21, 1979

[30] Foreign Application Priority Data

| Jul. 25, 1978 | [JP] | Japan | 53-101437[U] |
| Jul. 25, 1978 | [JP] | Japan | 53-101438[U] |
| Jul. 25, 1978 | [JP] | Japan | 53-101439[U] |
| Jul. 26, 1978 | [JP] | Japan | 53-101791[U] |

[51] Int. Cl.³ .......................................... B01D 29/14
[52] U.S. Cl. .................................. 210/336; 128/214 R
[58] Field of Search ............ 210/336, 23, 23 F, 23 H; 128/214 R

[56] References Cited

U.S. PATENT DOCUMENTS

| 3,660,281 | 5/1972 | Tober | 210/23 |
| 3,856,683 | 12/1974 | Parr | 210/336 |

FOREIGN PATENT DOCUMENTS

| 53-48392 | 5/1978 | Japan | 128/214 |
| 53-49885 | 5/1978 | Japan | 128/214 |

*Primary Examiner*—Frank A. Spear, Jr.
*Attorney, Agent, or Firm*—Armstrong, Nikaido, Marmelstein & Kubovcik

[57] ABSTRACT

A medical liquid dispensing device such as a medical administering dripset or a syringe having a liquid conducting tube comprising at least one partition element forming in the liquid conducting tube, at least two liquid passageways longitudinally separate from each other across the partition element, and at least one elongated microporous tubular element which extends in part in at least one of the two liquid passageways in the liquid conducting tube from the partition element. The tubular element has at least one longitudinal passageway closed in at least one of the liquid passageways in the liquid conducting tube. Thus, the microporous tubular element serves as a microporous filter medium for collecting on its inner and/or outer peripheral surfaces the solid particles contained in a liquid medicament or transfusion blood passed through the microporous tubular element.

21 Claims, 9 Drawing Figures

MEDICAL LIQUID DISPENSER WITH FILTER MEANS

FIELD OF THE INVENTION

The present invention relates to medical liquid dispensing devices, such as hypodermic, intramuscular or intravenous syringes or dripsets, used for injecting medical solutions or transfusing blood into body tissues or blood streams of human or animal bodies, or for drawing blood for transfusion from veins in human or animal bodies. More particularly, the present invention is concerned with a medical iquid dispensing device having a microporous filter medium capable of collecting fine solid particles from a liquid medicament or blood to be dispensed from or sucked into the liquid dispensing device.

BACKGROUND OF THE INVENTION

When handling syringes or dripsets for medical administering purposes, or during production or transport of such devices, there are a variety of possibilities wherein solid particles of, for example, dust can enter into the syringes or dripsets or into the liquids introduced into or stored in the syringes or dripsets. These particles may include not only dust or other fine particles which enter the syringes or dripsets from any external source, but also, fine fragments of glass or rubber which are produced when an ampoule or other breakable container of a liquid medicament is opened up or unsealed. Particles can also be formed during a process in which a rubber plug forming part of a dripset is fitted to a liquid reservoir or a liquid conducting tube of the dripset prior to practising a medical administering operation. When a medical solution or blood thus containing solid particles therein is introduced or transfused into a human or an animal body, the solid particles will find their way into the blood streams or body tissue and may injure the vascular tissue of the human or animal body.

Therefore, the provision of a filter medium in a syringe or a dripset for the purpose of separating fine solid particles from the liquid medicament or blood to be dispensed from the syringe or dripset has been proposed and practiced. The filter medium is usually located in the needle holder or the barrel of a syringe or can be located in the needle assembly of a dripset for collecting solid particles from the liquid medicament or the blood to be discharged from the syringe or the dripset through the cannula or injection needle attached to the syringe or forming part of the needle assembly of the dripset.

The filter medium thus incorporated into a syringe or a dripset is typically a fibrous gauze filter made of a woven fabric of, for example, nylon. A filter medium of this type is useful for collecting relatively large-sized solid particles such as, for example, the minute fragments of rubber which tend to be produced when a rubber plug having a liquid inlet needle inserted therethrough is forced into the neck portion of the plasic or glass bottle or vial of a dripset. The fibrous gauze filter is, however, not capable of collecting microscopically fine particles which may be deposited on the internal surfaces of the component elements of a syringe or a dripset. This allows such particles to pass through the filter medium into the vascular tissue of the patient to whom the administration using the syringe or dripset is to be conducted.

As is well known in the art, the sizes of the solid particles contained in or allowed in medical solutions or transfusion blood to be administered by syringes and dripsets usually range from the order of microns to the order of hundreds of microns in diameter. In order to collect solid particles having diameters of the order of microns at an acceptable efficiency by the use of a filter medium, the filter medium must be formed with pores, meshes or other voids measuring tenths of microns in diameter, length or width.

Attempts have therefore been made to provide microporous or micromesh filter media having pores, meshes or voids of such sizes. These attempts are largely directed at improving the quality of filter materials by making the filter materials denser having finer pores or meshes. For example, a micromesh filter of nylon, presently available on a commercial basis, is made up of densely interwoven nylon yarns of a minimum count or of warps and wefts which have different counts. Another example of the microporous or micromesh filter media which are in use today for medical administration purposes is a so-called membrane filter which consists of a disc or an otherwise shaped mat of sintered nylon powder.

While these known filter media are successful in collecting solid particles which are far smaller than before, problems are still encountered in that filter media tend to be clogged and cause deterioration of the filtering efficiency during use of the filter media. In certain situations, the filter medium per se becomes a source of impurities if the filter medium, such as a disc of sintered nylon powder, is partially fractured or fissured by the pressure of the liquids to be passed therethrough.

When, on the other hand, a filter medium is to be used for a medical administering dripset, it is preferred that the filter medium be provided in a flexible liquid conducting tube forming part of the dripset. Due to the limitation in the inside diameter of the tube, however, difficulties are experienced in mounting and positioning the filter medium securely and correctly in the tube. If the filter medium fails to be securely mounted or corrected positioned in the liquid conducting tube, the filter medium may lose its function or may at least be unable to exhibit its potential capabilities and preformance efficiency. If, furthermore, the filter medium provided in a liquid conducting tube of a medical administering dripset has pores or meshes having sizes so as to collect particles which are microscopically fine, the filter medium sized to be compatible with the fluid conducting tube will be easily clogged by the particles. This causes a reduction in the filtering efficiency thereof during use of the dripset. The reduction in the filtering efficiency of the filter medium results in a decrease in the flow rate of liquid through the liquid conducting tube in which the filter medium is provided. If the filtering efficiency of the filter medium used in a medical liquid dispensing device is reduced to a critical degree, the patient under administration may be exposed to a danger to life. In order to avoid such a danger, a compromise must be made by sacrificing the filtering efficiency for prevention of the clogging of the filter medium. A conventional microporous or micromesh filter medium for use in the liquid conducting tube of a medical administering dripset is, for this reason, actually capable of collecting only macroscopically sized particles out of the solid particles contained in the liquid to be passed through the tube.

The present invention is based on a discovery that all of these problems encountered in prior-art microporous or micromesh filter media for use in medical liquid dispensing devices can be eliminated by the use of a hollow microporous filament as a filter element.

As is well known in the art, a hollow microporous filament used mainly in the field of textiles is formed of polyvinylalcohol (PVA) or a rayon fiber and has inside and outside diameters of the order of hundreds of microns and pore sizes ranging from microns to tens of tenths of a micron. Such hollow microporous filaments have thus far been used not only as textile materials but as filter elements in some fields of chemical and biochemical industries for the separation of a polydisperse colloid into substances having different molecular dimensions. As a means for separating macromolecular and micromolecular substances from each other, for example, a hollow microporous filament is used for the demineralization and refining of an enzyme or the demineralization of hormone liquor in the field of biochemistry. When applied to the separation of micromolecular and micium-molecular substances from each other, a hollow microporous filament is utilized for the hypochlorization of soy sauce. In the separation, furthermore, of micromolecular substances from a mixed solution thereof, a hollow microporous filament is used for reclaiming an acid or alkali substance from the waste liquor produced in an electroplating process. In any of these known filter devices using hollow microporous filaments, however, such problems that are encountered in microporous filters for use in medical liquid dispensing devices as previously pointed out are usually not encountered. Even if the problems might be encountered, the problems would be far less serious than in the case of the medical liquid dispensing devices in which the dimensions of the spaces available for accommodating the filters are subject to an exacting limitation.

To use a hollow microporous filament of the above described nature as a filter element in a medical liquid dispensing device has been known per se from, for example, Japanese Provisionally Published Patent Specifications No. 53-48392 and No. 53-49885. In a medical liquid dispensing device shown in each of these provisionally published patent specifications, an elongated, hollow microporous filament which is open at one end and closed at the other is secured at the open end to a joint element having a passageway with which the passageway in the microporous filament communicates through the open end of the filament. The joint element is fitted to an end portion of a flexible liquid conducting tube of a medical administering dripset so that the hollow microporous filament axially projects from one end portion of the joint element into the passageway in the liquid conducting tube. The liquid medicament or the transfusion blood directed under pressure into the liquid conducting tube from a vertically inverted bottle held in a raised position is passed through the microscopic pores in the hollow microporous filament into the passageway in the microporous filament and through the passageway in the filament into the passageway in the joint element. The solid particles which may be contained in the liquid medicament or transfusion blood entering the hollow microporous filament are in this fashion collected on the outer peripheral surface of the filament projecting into the liquid conducting tube.

The hollow microporous filament thus arranged in a prior-art medical administering dripset serves not only as a filter element but as a microscopically perforated partition element between the passageway upstream of the microporous filament and the passageway downstream of the filament. In order for the hollow microporous filament thus serving as a partition element to play the part of a filter element in the liquid conducting tube, the passageway in the liquid conducting tube must be larger in cross sectional area than the hollow microporous filament so that the microporous filament has its particle-collecting outer peripheral surface exposed over the total area thereof to the liquid in the liquid conducting tube. If, in this instance, the hollow microporous filament is fitted to the joint element in such a manner that the filament has its open end portion received in an end portion of the passageway in the joint element, as is the case with the prior-art device under consideration, the passageway downstream of the hollow microporous filament becomes smaller in cross sectional area than the passageway upstream of the microporous filament. By reason of the difference thus existing between the cross sectional areas of the respective passageways upstream and downstream of the hollow microporous filament, the flow rate of liquid through the passageway downstream of the microporous filament becomes higher than the flow rate of liquid through the passageway upstream of the filament. When a liquid medicament or transfusion blood is passed through the hollow microporous filament, therefore, there is created a differential pressure between the respective passageways upstream and downstream of the microporous filament. The differential pressure acts through the microscopic pores in the hollow microporous filament on the solid particles which have collected on the outer peripheral surfaces of the microporous filament and, thus, urge the particles to move toward the passageway in the filament. As a consequence, those solid particles on the outer peripheral surface of the hollow microporous filament which are approximately equal in size or slightly larger than the microscopic pores in the microporous filament may be forced into the pores open at the outer peripheral surface of the filament or may be allowed to enter the passageway in the filament through the pores in the filament. This causes clogging of the microporous filament at the outer peripheral surface of the filament or results in reduction in the effective range of the sizes of the particles which can be collected by the hollow microporous filament serving as a filter element.

Another important drawback inherent in the prior-art device which disclosed in each of the patent specifications hereinbefore referred to, is that the hollow microporous filament of the device is held in position within the liquid conducting tube by the use of the joint element which connects the liquid conducting tube to another liquid conducting member or to the needle assembly included in the liquid dispensing device. Furthermore, provision of the joint element for the mounting of the filter element adds to the complexity of the overall configuration of the dripset and to the number of the steps to be taken by the practiser of the administration when in handling of the dripset.

Because, of the fact that the hollow microporous filament used in the prior-art medical liquid dispensing device is arranged to serve not only as a filter element but also as a partition element as previously mentioned, the filter element is capable of collecting solid particles only from the liquid entering the filter element from the passageway upstream of the filter element. For this reason, the hollow microporous filament serving as the filter element is permitted to collect solid particles only on its outer peripheral surface. As a consequence, the inner peripheral surface of the microporous filament is used merely as a surface to emit the filtered liquid into the passageway in the filament. Thus, the liquid medicament or the transfusion blood passed through the hollow microporous filament is filtered only once by the microporous filament. Thus the solid particles contained in the liquid medicament or blood have only one chance of being removed from the medicament or blood by the filter element of the microporous filament.

The present invention contemplates resolution of these problems inherent in prior-art liquid dispensing devices having filter elements, especially those using hollow microporous filaments.

SUMMARY OF THE INVENTION

In accordance with the present invention, there is provided a medical liquid dispensing device comprising an elongated, hollow liquid conducting member, at least one partition element securely held in position within the liquid conducting member and forming in the liquid conducting member at least two liquid passageways which are longitudinally separate from each other across the partition element, and at least one microporous tubular element which extends in part in at least one of the above mentioned two liquid passageways and which is formed with at least one longitudinal passageway which is closed to at least one of the aforesaid passageways in the liquid conducting member.

The passageway in the microporous tubular element serving as a filter medium in the medical liquid dispensing device thus constructed and arranged basically may be open to one of the liquid passageways in the liquid conducting member and closed in the other of the liquid passageways in the liquid conducting member. In this instance, the passageway in the tubular element may be open at one end thereof to one of the liquid passageways in the liquid conducting member and closed at the other end thereof in the other of the liquid passageways in the liquid conducting member or may be open at both ends thereof to one of the liquid passageways in the liquid conducting member. As an alternative, the passageway in the microporous tubular element in the medical liquid dispensing device having the above described basic construction may be closed in both of the liquid passageways in the liquid conducting member.

According to another and more specific aspect of the present invention, there is provided a medical liquid dispensing device which comprises an elongated, hollow liquid conducting member, at least to partition elements which are securely held in position within the liquid conducting member and which are longitudinally spaced apart from each other for forming in the liquid conducting member at least three separate liquid passageways consisting of an incoming liquid passageway longitudinally extending outwardly from one of the two partition elements, an outgoing liquid passageway longitudinally extending outwardly from the other of the partition elements, and an intermediate liquid passageway longitudinally extending between the two partition elements, and at least one microporous tubular element which longitudinally extends in part in the intermediate liquid passageway and which is formed with at least two longitudinal passageways which are separate from each other in the intermediate liquid passageway in the liquid conducting member.

In the medical liquid dispensing device thus constructed and arranged, one of the two passageways in the microporous tubular element may be either open or closed in the incoming liquid passageway in the liquid conducting member and the other of the passageways in the tubular element may be, likewise, either open or closed in the outgoing liquid passageway in the liquid conducting member.

DESCRIPTION OF THE PREFERRED EMBODIMENTS

Figures 1, 2:
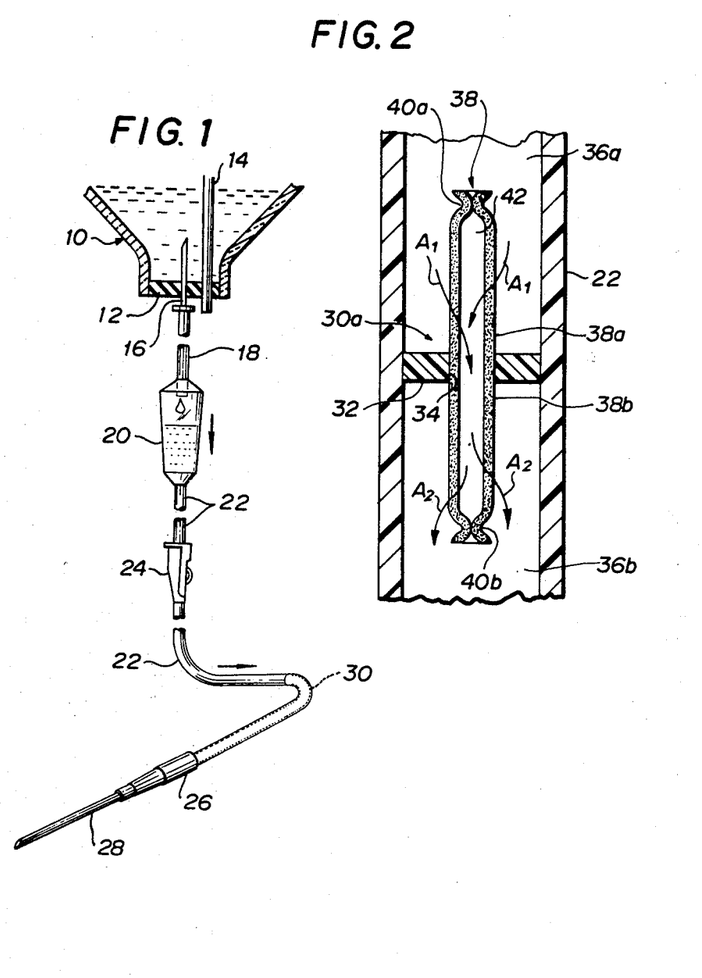
FIG. 1 is a perspective view showing a medical administering dripset including a liquid dispensing device provided by the present invention.
FIG. 2 is a longitudinal sectional view showing a first embodiment of the medical liquid dispensing device according to the present invention.

Referring to the drawings, first particularly to FIG. 1 thereof, the present invention is shown embodied in a medical administering dripset by way of example although the invention may be applied to a syringe of any type. The dripset is used in combination with an internally sterile liquid storage bottle 10 which can be made of glass or a transparent or transluscent plastic. A suitable liquid medicament or blood for transfusion is stored therein. The liquid storage bottle 10 is, when in use, vertically inverted with its neck portion at the bottom and is held in position raised above the level at which the liquid medicament or the blood for transfusion is to be discharged from the dripset. The neck portion of the bottle 10 is closed by a suitable closure such as a rubber plug 12. An air vent conduit or pipe 14 extends through the rubber plug 12 upwardly into the bottle 10 and is open at its upper end (not shown) above the surface of the liquid medicament or the transfusion blood in the bottle 10. The air vent conduit or pipe 14 is also open at the lower end thereof so that communication is provided between the open air and the open or vacant space (not shown) above the surface of the stored liquid medicament or blood for transfusion. Thus, the air vent conduit or pipe 14 is used to prevent development of a subatmospheric pressure in the open or vacant space in the bottle 10 when the liquid stored in the bottle is gradually consumed during use of the dripset, as is well known in the art.

The dripset per se further comprises a liquid inlet needle 16 which extends through the rubber plug 12 upwardly into the neck portion of the bottle 10. The liquid inlet needle 16 has its upper end in the liquid medicament or transfusion blood in the bottle 10 so that the liquid medicament or blood enters the needle 16 as long as the surface of the medicament or blood is maintained above the open upper end of the needle 16. The liquid inlet needle 16 thus fitted to the rubber plug 12 of the liquid storage bottle 10 has a flexible liquid conducting tube 18 fitted to its lower end. A liquid reservoir 20 adapted to have temporarily stored therein the liquid medicament or blood continuously supplied thereto from the liquid storage bottle 10 is suspended and connected to the tube 18. The liquid reservoir 20 in turn has a flexible liquid conducting tube 22 fitted to its lower end which is shown provided with an adjustable clamp 24. As is well known in the art, the adjustable clamp 24 is attached to the liquid conducting tube 22 for collapsing the clamped portion of the tube 22 in such a manner that the passageway in the clamped portion is closed when the dripset is not in use or the passageway is reduced in cross section to provide a desired flow rate of liquid therethrough when the dripset is in use. The liquid conducting tube 22 has a needle assembly 26 including a detachable injection needle 28 fitted at its leading end. Each of the liquid conducting tubes 18 and 22 is formed of a suitable thermoplastic synthetic resin such as, for example, plasticized polyvinyl chloride or high-pressure-process polyethylene. If desired, the liquid reservoir 20 shown may be dispensed with so that the liquid conducting tube 22 connected at one end to the needle assembly 28 is fitted directly to the liquid inlet needle 16.

The construction and arrangement of the medical administering dripset per se, as above described and shown in FIG. 1, is well known in the art and is merely representative of those of the various types of medical liquid dispensing devices which include not only dripsets but syringes. Thus, the present invention may be applied to any syringe, medical administering dripset and other medical liquid dispensing device which are known per se.

In accordance with the present invention, there is provided in the medical administering dripset illustrated in FIG. 1 a filter unit 30 indicated schematically by dotted lines and shown, by way of example, to be disposed in the liquid conducting tube 22 intervening between the liquid reservoir 20 and the needle assembly 26 of the dripset. Description will be hereinafter made regarding preferred examples of the detailed construction and arrangement of the filter unit 30 with reference to FIGS. 2 to 9.

Referring to FIG. 2, the filter unit, generally designated by 30a is shown comprising a partition element 32 which is in the form of an annular disc formed with an aperture 34 and which is securely attached along its outer peripheral end to the inner peripheral surface of the liquid conducting tube 22. The partition element 32 is formed of a suitable thermoplastic synthetic resin such as, plasticized or unplasticized polyvinylchloride, and is bonded to the inner peripheral surface of the liquid conducting tube 22 with a suitable organic adhesive. Two liquid passageways are formed in the tube 22 by the partition element 32. These consist of an incoming liquid passageway 36a longitudinally extending in one direction from or, in the arrangement herein shown, upstream of the partition element 32 and an outgoing liquid passageway 36b longitudinally extending in the other direction or, in the arrangement herein shown, downstream of the partition element 32. An elongated microporous tubular element 38 constituted by a hollow microporous filament is passed through the aperture 34 in the partition 32. The element 38 has a liquid inlet longitudinal portion 38a axially extending in the incoming liquid passageway 36a and a liquid outlet longitudinal portion 38b axially extending in the outgoing liquid passageway 36b. The liquid inlet and outlet longitudinal portions 38a and 38b of the tubular element 38 are collapsed at or adjacent to the respective leading ends of the portions as indicated at 40a and 40b, respectively. Thus a continuous longitudinal passageway closed at both ends thereof is formed in the tubular element 38. The tubular element 38 is secured to the partition element 32 by a suitable organic adhesive so that the incoming and outgoing liquid passageways 36a and 36b in the liquid conducting tube 22 are separated from each other hermetically by the partition element 32 closely fitted to the inner peripheral surface of the liquid conducting tube 22 and macroscopically by the microporous tubular element 38.

When a liquid medicament or blood for transfusion supplied from the liquid storage bottle 10 in the dripset arrangement shown in FIG. 1 is directed under pressure into the liquid conducting tube 22 shown in FIG. 2, the medicament or blood admitted into the incoming liquid passageway 36a passes through the microscopic pores in the liquid inlet longitudinal portion 38a of the microporous tubular element 38 into the longitudinal passageway 42 in the tubular element 42 as indicated by arrows $A_1$. The medicament or blood is thereafter passed from the passageway 42 in the tubular element 38 into the outgoing liquid passageway 36b in the liquid conducting tube 22 through the microscopic pores in the liquid outlet longitudinal portion 38b of the tubular element 38 as indicated by arrows $A_2$. When the liquid medicament or the blood for transfusion enters the passageway 42 in the tubular element 38 through the microscopic pores in the liquid inlet longitudinal portion 38a of the tubular element 38, the fine solid particles contained in the liquid medicament or blood which are larger in size than the pores are deposited on the outer peripheral surface of the particular portion 38a of the tubular element 38. When the liquid medicament or blood thus admitted into the passageway 42 in the tubular element 38 is being withdrawn from the passageway 42 into the outgoing liquid passageway 36b in the liquid conducting tube 22 through the microscopic pores in the liquid outlet longitudinal portion 38b of the tubular element 38, the fine solid particles which may have been allowed to pass through the pores in the liquid inlet longitudinal portion 38a of the tubular element 38 are largely collected on the inner peripheral surface of the particular portion 38b of the tubular element 38. The liquid medicament or the blood for transfusion directed into the liquid conducting tube 22 is in this manner filtered twice. That is, it is filtered first primarily by the liquid inlet longitudinal portion 38a and then secondarily by the liquid outlet longitudinal portion 38b of the microporous tubular element 38. The resultant clean liquid medicament or blood for transfusion is directed through the outgoing liquid passageway 36b in the liquid conducting tube 22 toward the needle assembly 26 in the dripset arrangement illustrated in FIG. 1.

It will be apparent that the filter unit 30a forming part of the embodiment hereinbefore described with reference to FIG. 2 may be modified so that the microporous tubular element constituted by a hollow microporous filament axially projects into only one of the incoming and outgoing liquid passageways 36a and 36b in the liquid conducting tube 22 although an embodiment including such a modified filter unit is not shown in the drawings. In this modified form of filter unit, the passageway in the microporous tubular element is open at one end thereof in one of the incoming and outgoing liquid passageways 36a and 36b and closed at the or adjacent to the other end in the other of the passageways 36a and 36b in the liquid conducting tube 22. The liquid medicament or the blood for transfusion directed into the liquid conducting tube 22 provided with the filter unit thus arranged is filtered only once by the microporous tubular element of the filter unit when the liquid medicament or transfusion blood passes from the incoming liquid passageway 36a in the liquid conducting tube 22 into the passageway in the tubular element or from the passageway in the tubular element into the outgoing liquid passageway 36b in the tube 22 through the microscopic pores in the tubular element.

While the liquid conducting tube 22 provided with the filter unit 30a in the embodiment illustrated in FIG. 2 or the above described modification of the filter unit 30a is divided into only two separate liquid passageways 36a and 36b by the single partition element 32, the liquid conducting tube 22 forming part of a medical liquid dispensing device according to the present invention may be divided into three or more separate liquid passageways by two or more partition elements. The liquid medicament or the transfusion blood directed into the liquid conducting tube 22 is filtered twice or more when passed through the individual liquid passageways. FIGS. 3 to 6 show embodiments each having a liquid conducting tube having three liquid passageways separated from each other by first and second partition elements 32a and 32b which are securely held in position within the liquid conducting tube 22 and which are longitudinally spaced apart from each other for forming the three liquid passageways therebetween. The partition elements 32a and 32b are formed with apertures 34a and 34b, respectively, which are axially aligned with each other.

Figure 3:
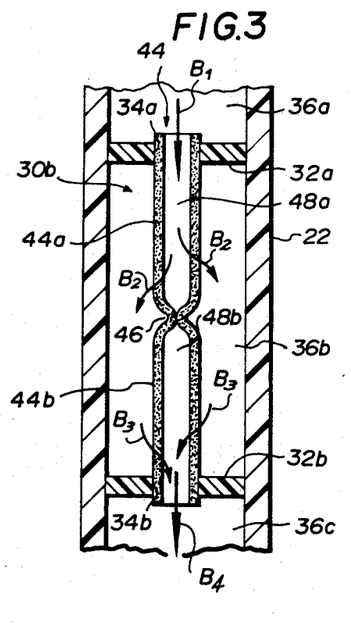
FIG. 3 is a longitudinal sectional view showing a second embodiment.

The partition elements 32a and 32b in the embodiment illustrated in FIG. 3 form part of a filter unit 30b which is adapted to twice filter the liquid to be passed therethrough. The three liquid passageways formed in the liquid conducting tube by such partition elements 32a and 32b consist of an incoming liquid passageway 36a longitudinally extending outwardly from or upstream of the first partition element 32a, an intermediate liquid passageway 36b longitudinally extending between the first and second partition elements 32a and 32b, and an outgoing liquid passgeway 36c longitudinally extending outwardly from or downstream of the second partition element 32b. An elongated microporous tubular element 44 constituted by a single hollow microporous filament is passed through the respective apertures 34a and 34b in the first and second partition elements 32a and 32b. The microporous tubular element 44 is collapsed at its longitudinally intermediate portion 46 in the intermediate liquid passageway 36b. The element 44 has a liquid inlet longitudinal portion 44a secured to the first partition element 32a and longitudinal passageway 48a which is closed at the collapsed end 46 of the longitudinal portion 44a and which is open at the other end of the portion 44a in the incoming liquid passageway 36a in the liquid conducting tube 22. The element 44 further has a liquid outlet longitudinal portion 44b secured to the second partition element 32b having a longitudinal passageway 48b which is closed at the collapsed end 46 of the longitudinal portion 44b and which is open at the other end in the outgoing liquid passageway 36b in the liquid conducting tube 22. The tubular element 44 thus configured is secured to the first and second partition elements 32a and 32b through the apertures 34a and 34b in the partition elements 32a and 32b, respectively, by a suitable organic adhesive. Thus the three liquid passageways 36a, 36b and 36c in the liquid conducting tube 22 are separated from each other hermetically by the partition elements 32a and 32b closely fitted to the inner peripheral surface of the liquid conducting tube 22 and macroscopically by the microporous tubular element 44.

When the liquid medicament or the transfusion blood supplied from the liquid storage bottle 10 in the dripset arrangement illustrated in FIG. 1 is directed under pressure into the liquid conducting tube 22 shown in FIG. 3, the medicament or blood is first admitted into the incoming liquid passageway 36a in the tube 22 and further into the longitudinal passageway 48a in the liquid inlet longitudinal portion 44a of the microporous tubular element 44 as indicated by an arrow $B_1$. The liquid passes through the microscopic pores in the longitudinal portion 44a of the tubular element 44 into the intermediate liquid passageway 36b in the liquid conducting tube 22 as indicated by arrows $B_2$. The liquid medicament or the transfusion blood passes through the microscopic pores in the liquid outlet longitudinal portion 44b of the tubular element 44 into the longitudinal passageway 44b in the portion 44b of the tubular element 44 as indicated by arrows $B_3$. It then flows from the passageway 48b into the outgoing liquid passageway 36c in the liquid conducting tube 22 as indicated by an arrow $B_4$. Thus, the fine solid particles originally contained in the liquid medicament or the transfusion blood in the incoming liquid passageway 36a in the liquid conducting tube 22 are deposited primarily on the inner peripheral surface of the liquid inlet longitudinal portion 44a of the microporous tubular element 44 and thereafter secondarily on the outer peripheral surface of the liquid outlet longitudinal portion 44b of the tubuar element 44. The liquid medicament or the transfusion blood which has been twice filtered by the microporous tubular element 44 is directed through the outgoing liquid passgeway 36b in the liquid conducting tube 22 toward the needle assembly 26 in the dripset arrangement illustrated in FIG. 1.

Figure 4:
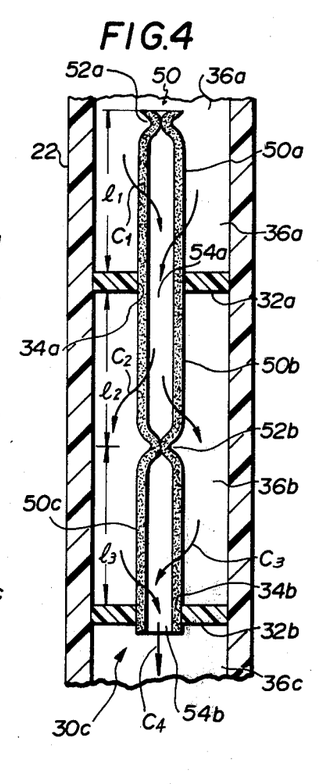
FIG. 4 is a longitudinal sectional view showing a third embodiment.

Turning to FIG. 4 of the drawings, the two partition elements 32a and 32b forming three separate liquid passageways 36a, 36b and 36c in the liquid conducting tube 22 as in the embodiment hereinbefore described with reference to FIG. 3 form part of a filter unit 30c which is adapted to thrice filter the liquid passed therethrough. The filter unit 30c further includes a microporous tubular element 50 which is passed through the respective apertures 34a and 34b in the first and second partition elements 32a and 32b. The element 50 is collapsed at or adjacent to its end 52a in the incoming liquid passageway 36a in the liquid conducting tube 22 and at its longitudinally intermediate point or portion 52b in the intermediate liquid passageway 36b in the liquid conducting tube 22. Thus, the microporous tubular element 50 forming part of the filter unit 30c illustrated in FIG. 4 has a primary liquid inlet longitudinal portion 50a longitudinally extending outwardly from or upstream of the first partition element 32a and terminating at the collapsed end 52a of the tubular element 50, a primary liquid outlet longitudinal portion 50b longitudinally extending inwardly from or downstream of the first partition element 32a and terminating at the collapsed intermediate point or portion 52b of the tubular element 50, and a secondary liquid inlet and outlet longitudinal portion 50c longitudinally extending inwardly from or upstream of the second partition element 32b and terminating at the collapsed intermediate point or portion 52b of the tubular element 50. The microporous tubular element 50 thus composed of the three longitudinal portions 50a, 50b and 50c has a first passageway 54a formed in the primary liquid inlet and outlet longitudinal portions 50a and 50b and a second passageway 54b formed in the secondary liquid inlet and outlet longitudinal portion 50c of the tubular element 50. The first passageway 54a formed in the primary liquid inlet and outlet longitudinal portions 50a and 50b continuously extends between and is closed at the collapsed end 52a of the longitudinal portion 50a and the collapsed intermediate point or portion 52b between the primary liquid outlet longitudinal portion 50b and the secondary liquid inlet and outlet longitudinal portion 50c of the tubular element 50. The second passageway 54b formed in the secondary liquid inlet and outlet longitudinal portion 50c is closed at the collapsed intermediate point or portion 52b and is open to the outgoing liquid passageway 36c in the liquid conducting tube 22 at its end opposite to the collapsed intermediate point or portion 52b.

When a liquid medicament or blood for transfusion is supplied under pressure into the liquid conducting tube 22 provided with the filter unit 30c thus constructed and arranged, the medicament or blood admitted into the incoming liquid passageway 36a in the tube 22 passes through the microscopic pores in the primary liquid inlet longitudinal portion 50a of the microporous tubular element 50 into the continuous passageway 54a in the primary liquid inlet and outlet longitudinal portions 50a and 50b of the tubular element 50 as indicated by arrows $C_1$. The liquid medicament or the transfusion blood thus admitted into the passageway 54a continuously extending in the longitudinal portions 50a and 50b of the tubular element 50 passes through the microscopic pores in the primary liquid outlet longitudinal portion 50b of the tubular element 50 into the intermediate liquid passageway 36b in the liquid conducting tube 22 as indicated by arrows $C_2$, and further through the microscopic pores in the secondary liquid inlet and outlet longitudinal portion 50c of the tubular element 50 into the second passageway 54b in the longitudinal portion 50c as indicated by arrows $C_3$. The liquid medicament or the blood which has entered the passageway 54b in the secondary liquid inlet and outlet longitudinal portion 50c of the tubular element 50 flows from the passageway 54b into the outgoing liquid passageway 36c in the liquid conducting tube 22 as indicated by an arrow $C_4$ and is directed through the outgoing liquid passageway 36c of the tube 22 toward the needle assembly 26 in the dripset arrangement illustrated in FIG. 1. The fine solid particles originally contained in the liquid medicament or transfusion blood passed through the filter unit 30c of the embodiment shown in FIG. 4 are deposited primarily on the outer peripheral surface of the primary liquid inlet longitudinal portion 50a, secondarily on the inner peripheral surface of the primary liquid outlet portion 50i b and tertiarily on the outer peripheral surface of the secondary liquid inlet and outlet longitudinal portion 50c of the microporous tubular element 50.

Figure 5:
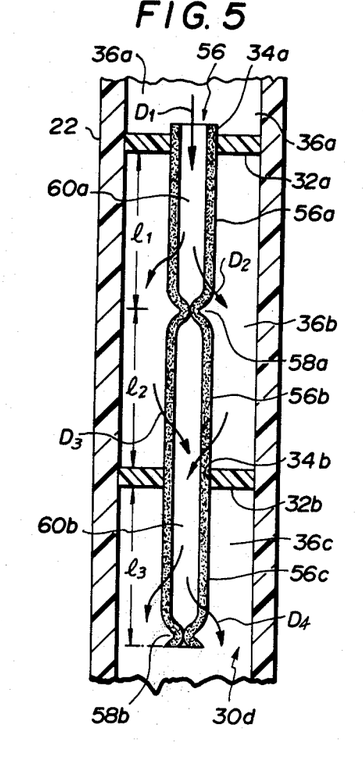
FIG. 5 is a longitudinal sectional view showing a fourth embodiment.

The embodiment illustrated in FIG. 5 has provided therein a filter unit 30d having a microporous tubular element 56 which is configured similarly to the microporous tubular element 50 of the filter unit 30c in the embodiment of FIG. 4 but which is arranged in the opposite direction with respect to the direction of flow of the liquid to be passed through the liquid conducting tube 22. The microporous tubular element 56 forming part of the filter unit 30d thus arranged is collapsed at its longitudinally intermediate point or portion 58a in the intermediate liquid passageway 36b in the liquid conducting tube 22 and at or adjacent to its end 58b in the outgoing liquid passageway 36c in the tube 22. Accordingly, the microporous tubular element 56 has a primary liquid inlet and outlet longitudinal portion 56a longitudinally extending inwardly from or downstream of the first partition element 32a and terminating at the collapsed intermediate point or portion 58a of the tubular element 56, a secondary liquid inlet longitudinal portion 56b longitudinally extending inwardly from or upstream of the second partition element 32b and terminating at the collapsed intermediate point or portion 58a of the tubular element 56, and a secondary liquid outlet longitudinal portion 56c longitudinally extending outwardly from or downstream of the second partition element 32b and terminating at the collapsed end 58b of the tubular element 56 as shown. The microporous tubular element 56 thus composed of the three longitudinal portions 56a, 56b and 56c has a first passageway 60a formed in the primary liquid inlet and outlet longitudinal portion 56a of the tubular element 56 and a second passageway 60b formed in the secondary liquid inlet and outlet longitudinal portions 56b and 56c of the tubular element 56. The first passageway 60a formed in the primary liquid inlet longitudinal portion 56a is open at one end to the incoming liquid passageway 36a in the liquid conducting tube 22 and is closed at the collapsed intermediate point or portion 58a of the tubular element 56. The second passageway 60b formed in the secondary liquid inlet and outlet longitudinal portions 56b and 56c continuously extends between and is closed at the collapsed intermediate point or portions 58a and the collapsed end 58b of the tubular element 56.

When a liquid medicament or blood for transfusion is supplied under pressure into the liquid conducting tube 22 provided with the filter unit 30d thus constructed and arranged, the medicament or blood is directed into the incoming liquid passageway 36a in the tube 22 and further into the first passageway 60a in the primary liquid inlet and outlet longitudinal portion 56a of the microporous tubular element 56 as indicated by an arrow $D_1$. The liquid medicament or blood thus admitted into the passageway 60a in the tubular element 56 passes through the microscopic pores in the primary liquid inlet and outlet longitudinal portion 56a of the tubular element 56 into the intermediate liquid passageway 36b in the liquid conducting tube 22 as indicated by arrows $D_2$ and further through the microscopic pores in the secondary liquid inlet longitudinal portion 56b of the tubular element 56 into the second passageway 60b continuously extending in the secondary liquid inlet and outlet longitudinal portions 56b and 56c of the tubular element 56 as indicated by arrows $D_3$. The liquid medicament or the blood which has thus entered the second passageway 60b in the tubular element 56 further passes through the microscopic pores in the secondary liquid outlet longitudinal portion 56c of the tubular element 56 into the outgoing liquid passageway 36c in the liquid conducting tube 22 as indicated by an arrow $D_4$. The fine solid particles originally contained in the liquid medicament or transfusion blood passed through the filter unit 30d are deposited primarily on the inner peripheral surface of the primary liquid inlet and outlet longitudinal portion 56a, secondarily on the outer peripheral surface of the secondary liquid inlet longitudinal portion 56b, and tertiarily on the inner peripheral surface of the secondary liquid outlet longitudinal portion 56c of the microporous tubular element 56.

In each of the embodiments hereinbefore described with reference to FIGS. 4 and 5, the filtering efficiency of the filter unit 30c (FIG. 4) or the filter unit 30d (FIG. 5) can be selected by selecting the inside and outside diameters of the microporous hollow filament to be used as the microporous tubular element 50 in the filter unit 30c or the microporous tubular element 56 in the filter unit 30d, the lengths $l_1$, $l_2$ and $l_3$ of the individual longitudinal portions 50a, 50b and 50c, respectively, of the tubular element 50 or the individual longitudinal portions 56a, 56b and 56c, respectively, of the tubular element 56, and the average sizes of the microscopic pores in the tubular element 50 or 56.

Figure 6:
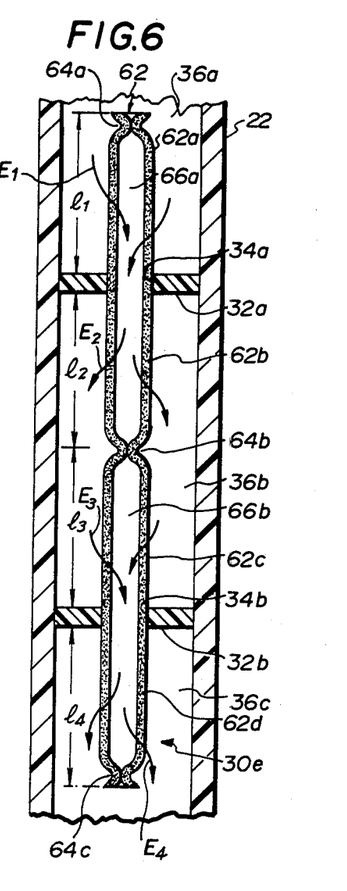
FIG. 6 is a longitudinal sectional view showing a fifth embodiment.

A filter unit 30e is provided in the embodiment illustrated in FIG. 6 which is adapted to filter the liquid passed therethrough four times. Such a filter unit 30e comprises, in addition to the first and second partition elements 32a and 32b forming the three separate liquid passageways 36a, 36b and 36c in the liquid conducting tube 22, an elongated microporous tubular element 62 longitudinally passed through the respective apertures 34a and 34b in the partition elements 32a and 32b and longitudinally extending in part in the incoming liquid passageway 36a, in part in the intermediate liquid passageway 36b and in part in the outgoing liquid passageway 36c in the liquid conducting tube 22. The microporous tubular element 62 is collapsed at or adjacent to its first end 64a in the incoming liquid passageway 36a, at its longitudinally intermediate point or portion 64b in the intermediate liquid passageway 36b, and at its second end 64c in the outgoing liquid passageway 36c in the liquid conducting tube 22. Thus, the microporous tubular element 62 forming part of the filter unit 30e illustrated in FIG. 6 has a primary liquid inlet longitudinal portion 62a longitudinally extending outwardly from or upstream of the first partition element 32a and terminating at the first collapsed end 64a of the tubular element 62, a primary liquid outlet longitudinal portion 62b longitudinally extending inwardly from or downstream of the first partition element 32a and terminating at the collapsed intermediate point or portion 64b of the tubular element 62, a secondary liquid inlet longitudinal portion 62c longitudinally extending inwardly from or upstream of the second partition element 32b and terminating at the collapsed intermediate point or portion 64b of the tubular element 62, and a secondary liquid outlet longitudinal portion 62d longitudinally extending outwardly from or downstream of the second partition element 32b and terminating at the second collapsed end 64c of the tubular element 62 as shown. The microporous tubular element 62 is thus composed of the four discrete longitudinal portions 62a, 62b, 62c and 62d. The element 62 has a first passageway 66a formed in the primary liquid inlet and outlet longitudinal portions 62a and 62b and a second passageway 66b formed in the secondary liquid inlet and outlet longitudinal portions 62c and 62d of the tubular element 62. The first passageway 66a formed in the primary liquid inlet and outlet longitudinal portions 62a and 62b continuously extends between the first collapsed end 64a and the collapsed intermediate point or portion 64b of the tubular element 62. The second passageway 66b formed in the secondary liquid inlet and outlet longitudinal portions 62c and 62d continuously extends between the collapsed intermediate point or portion 64b and the second collapsed end 64c of the tubular element 62.

In using the filter unit 30e of FIG. 6, the liquid medicament or the transfusion blood supplied under pressure into the liquid conducting tube 22 from the liquid storage bottle 10 in the dripset arrangement illustrated in FIG. 1 is first directed into the incoming liquid passageway 36a in the liquid conducting tube 22 and passes through the microscopic pores in the primary liquid inlet longitudinal portion 62a into the first passageway 66a continuously extending in the primary liquid inlet and outlet longitudinal portions 62a and 62b of the tubular element 62, as indicated by arrows $E_1$. The liquid medicament or transfusion blood thus admitted into the passageway 66a in the microporous tubular element 62 thereafter passes through the microscopic pores in the primary liquid outlet longitudinal portion 62b of the tubular element 62 into the intermediate liquid passageway 36b in the liquid conducting tube 22 as indicated by arrows $E_2$ and from the liquid passageway 36b into the second passageway 64b in the tubular element 62 through the microscopic pores in the secondary liquid inlet longitudinal portion 62c of the tubular element 62 as indicated by arrows $E_3$. The liquid medicament or blood which has thus entered the passageway 66b continuously extending in the secondary liquid inlet and outlet longitudinal portions 62c and 62d of the tubular element 62 passes through the microscopic pores in the secondary liquid outlet longitudinal portion 62d of the tubular element 62 into the outgoing liquid passageway 36c in the liquid conducting tube 22 as indicated by arrows $E_4$ and is thereafter directed through the outgoing liquid passageway 36c of the tube 22 toward the needle assembly 26 in the dripset arrangement illustrated in FIG 1. The fine solid particles originally contained in the liquid medicament or the transfusion blood which has been passed through the filter unit 30e of the embodiment shown in FIG. 6 are deposited primarily on the outer peripheral surface of the primary liquid inlet longitudinal portion 62a, secondarily on the inner peripheral surface of the primary liquid outlet longitudinal portion 62b, tertiarily on the outer peripheral surface of the second liquid inlet longitudinal portion 62c, and finally on the inner peripheral surface of the second liquid outlet longitudinal portion 62d of the tubular element 62. In this embodiment the filtering efficiency of the filter unit 30e is selected by selecting the inside and outside diameters of the microporous hollow filament to be used as the microporous tubular element 62, and respective lengths $l_1$, $l_2$, $l_3$ and $l_4$ of the individual longitudinal portion 62a, 62b, 62c and 62d, respectively, and the average sizes and degree of distribution per unit volume of the microscopic pores in the microporous tubular element 62.

Figure 7:
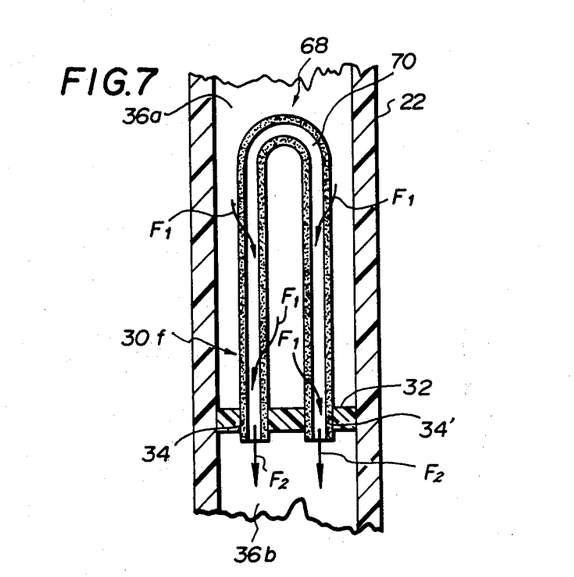
FIG. 7 is a longitudinal sectional view showing a sixth embodiment.

FIG. 7 shows still another preferred embodiment of the medical liquid dispensing device according to the present invention. The embodiment illustrated in FIG. 7 comprises a filter unit 30f including a partition element 32 which is formed with two apertures 34 and 34'. The partition element 32 is secured along its outer peripheral end to the inner peripheral surface of the liquid conducting tube 22 and forms in the tube 22 two liquid passageways consisting of an incoming liquid passageway 36a longitudinally extending in one direction from or upstream of the partition element 32 and an outgoing liquid passageway 36b longitudinally extending in the other direction from or downstream of the partition element 32 as in the embodiment illustrated in FIG. 3.

An elongated microporous tubular element 68 constituted by a microporous hollow filament extends from the partition element into the incoming liquid passageway 36a generally in a U-shaped configuration and has opposite end portions secured to the partition element 32 through the apertures 34 and 34', respectively. Thus, the microporous tubular element 68 forming part of the filter unit 30f has a longitudinal passageway 70 which is continuous throughout the length of the tubular element 68 and which is open at the opposite ends thereof to the outgoing liquid passageway 36b in the liquid conducting tube 22.

The U-shaped microporous hollow filament to constitute the microporous tubular element 68 for the filter unit 30f thus constructed and arranged may be obtained as one of the elements produced from a single elongated microporous hollow filament which is wound on a suitable member or structure having a rectangular or oval cross section while the hollow filament is extruded from an extrusion nozzle during production of the filament. This is done while the filament still remain in a plasticised state. The filament is thereafter cut into a number of segments along two lines transverse to the turns of the filament after the filament is set.

When a dripset having the filter unit 30f provided in the liquid conducting tube 22 is used, the liquid medicament or the transfusion blood supplied to the liquid conducting tube 22 flows into the incoming liquid passageway 36a in the tube 22. The liquid medicament or blood then passes through the microscopic pores in the U-shaped longitudinal portion of the microporous tubular element 68 into the longitudinal passageway 70 in the tubular element 68 as indicated by arrows $F_1$ and from the passageway 70 in the tubular element 68 into the outgoing liquid passageway 36b in the liquid conducting tube 22 as indicated by arrows $F_2$. The fine solid particles originally contained in the liquid medicament or the transfusion blood thus passed through the filter unit 30f are deposited on the outer peripheral surface of the U-shaped longitudinal portion of the microporous tubular element 68 extending in the incoming liquid passageway 36a of the liquid conducting tube 22 so that the liquid medicament or blood cleared of such particles enter the outgoing liquid passageway 36b in the liquid conducting tube 22.

The filter unit 30f in the above described embodiment may be modified to be inverted with respect to the direction of flow of liquid therethrough so that the U-shaped longitudinal portion of the microporous tubular element 68 projects from the partition element 32 into the outgoing liquid passageway 36b in the liquid conducting tube 22 and has its longitudinal passageway open at the opposite ends thereof to the incoming liquid passageway 36a in the liquid conducting tube 22, though not illustrated in the drawings.

While each of the embodiments of the present invention has been described and shown as using only one microporous tubular element in the filter unit of the embodiment, it should be borne in mind that such an assumption is not limitative of the subject matter of the present invention. Thus, the filter unit forming part of a medical liquid dispensing device according to the present invention may comprise two or more microporous tubular elements each of which is arranged similarly to the microporous tubular in any of the embodiments hereinbefore described and shown.

Figure 8:
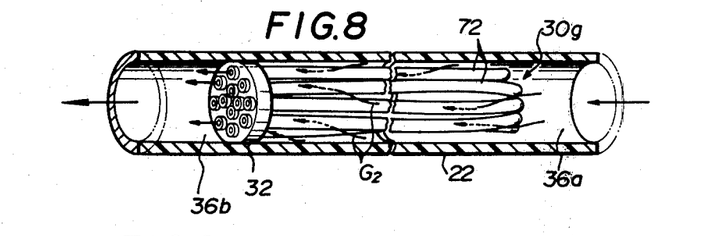
FIG. 8 is a longitudinal, partial sectional, partial plan view showing a seventh embodiment.

FIG. 8 shows an embodiment in which a filter unit 30g comprises a plurality of elongated microporous tubular elements 72 each having a generally U-shaped configuration and arranged similarly to the single microporous tubular element 68 forming part of the filter unit 30f included in the embodiment of FIG. 7. The individual tubular elements 72 extend each in a generally U-shaped configuration in the incoming liquid passageway 36a in the liquid conducting tube 22 and are jointly secured to a single partition element 32 formed with a plurality of apertures so that each of the tubular elements 72 is open at its opposite ends to the outgoing liquid passageway 36b in the liquid conducting tube 22.

Figure 9:
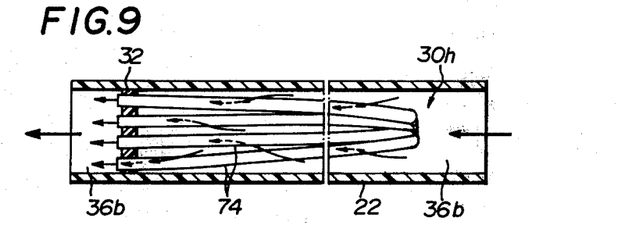
FIG. 9 is a longitudinal sectional view showing a modified form of the embodiment of FIG. 8.

The embodiment of FIG. 8 may be modified as shown in FIG. 9 wherein a filter unit 30h comprises a number of elongated microporous tubular elements 74 individually extending longitudinally in the incoming liquid passageway 36a in the liquid conducting tube 22 and jointly connected to a single partition element 32 formed with a number of apertures. Each of the microporous tubular elements 74 projects through these apertures in the partition element 32 for being open at one end to the outgoing liquid passageway 36b in the liquid conducting tube 22 and is closed at the opposite end thereof in the incoming liquid passageway 36a in the liquid conducting tube 22. The microporous tubular elements 74 may be collapsed at or adjacent their respective ends in the incoming liquid passageway 36a in the liquid conducting tube 22 but are assumed, by way of example, to be closed by a suitable adhesive, preferably an adhesive of a thermosetting resin such as an epoxy resin. It is apparent that such an adhesive may be utilized to close the microporous tubular element in any of the embodiments shown in FIGS. 2 to 6 in lieu of collapsing a portion or portions of the microporous tubular element.

Although, furthermore, it has been assumed that the liquid dispensing device embodying the present invention is to be incorporated into a medical administering dripset arranged as shown in FIG. 1, a medical liquid dispensing device according to the present invention may be applied to a dripset which is otherwise arranged, or to any of syringes and other liquid dispensing devices to be used for medical administering purposes. When a device according to the present invention is to be applied to a syringe, the filter unit to be provided in the syringe may be located in the cylindrical barrel or the needle holder of the syringe.

What is claimed is:

1. A medical liquid dispensing device comprising an elongated, hollow liquid conducting member, at least two partition elements which are securely held in position within said liquid conducting member and which are longitudinally spaced apart from each other for forming in the liquid conducting member at least three separate liquid passageways consisting of an incoming liquid passageway longitudinally extending outwardly from one of said two partition elements, an outgoing liquid passageway longitudinally extending outwardly from the other of the two partition elements, and an intermediate liquid passageway longitudinally extending between the two partition elements, and at least one microporous tubular element which longitudinally extends in part through said intermediate passageway and which is formed with at least two longitudinal passageways which are separate from each other in said intermediate liquid passageway in said liquid conducting member.

2. A medical liquid dispensing device as set forth in claim 1, in which one of said two longitudinal passageways in the microporous tubular element is open to said incoming liquid passageway in the liquid conducting member and the other of the two longitudinal passageways in the tubular element is open to said outgoing liquid passageway in the liquid conducting member.

3. A medical liquid dispensing device as set forth in claim 1, in which one of said two longitudinal passageways in the microporous tubular element is closed in said incoming liquid passageway in the liquid conducting member and the other of the two longitudinal passageways in the tubular element is open to said outgoing liquid passageway in the liquid conducting member.

4. A medical liquid dispensing device as set forth in claim 1, in which one of said two longitudinal passageways in the microporous tubular element is open to said incoming liquid passageway in the liquid conducting member and the other of the two longitudinal passageways in the tubular element is closed in said outgoing liquid passageway in the liquid conducting member.

5. A medical liquid dispensing device as set forth in claim 1, in which one of said two longitudinal passageways in the microporous tubular element is closed in said incoming liquid passageway in the liquid conducting member and the other of the two longitudinal passageways in the tubular element is closed in said outgoing liquid passageway in the liquid conducting member.

6. A medical liquid dispensing device as set forth in claim 1, in which said microporous tubular element has a first longitudinal portion extending from said incoming liquid passageway into said intermediate liquid passageway through one of said partition elements and formed with one of said two longitudinal passageways and a second longitudinal portion extending from said outgoing liquid passageway into the intermediate liquid passageway through the other of said partition elements and formed with the other of said two longitudinal passageways, wherein the microporous tubular element is collapsed between the first and second longitudinal portions thereof so that each of the respective passageways in the first and second longitudinal portions of the tubular element is closed at one end in the intermediate liquid passageway in the liquid conducting member.

7. A medical liquid dispensing device as set forth in claim 6, in which the respective passageways in said first and second longitudinal portions of said microporous tubular element are open at the other ends thereof to the incoming and outgoing liquid passageways, respectively, in said liquid conducting member.

8. A medical liquid dispensing device as set forth in claim 1, in which said microporous tubular element has a first longitudinal portion longitudinally extending from one of said partition elements into said incoming liquid passageway in the liquid conducting member, a second longitudinal portion extending from said one of the partition elements into said intermediate liquid passageway in the liquid conducting member, and a third longitudinal portion extending from the other of said partition elements into said intermediate liquid passageway in the liquid conducting member, wherein one of said two longitudinal passageways in the microporous tubular element is formed and continuous in the first and second longitudinal portions of the tubular element and the other of the two longitudinal passageways in the tubular element is formed in the third longitudinal portion of the tubular element and wherein the microporous tubular element is collapsed between the second and third longitudinal portions thereof so that each of the longitudinal passageways in the tubular element is closed at one end in the intermediate liquid passageway in the liquid conducting member.

9. A medical liquid dispensing device as set forth in claim 8, in which the passageway continuous in said first and second longitudinal portions of said microporous tubular element is closed at the other end thereof in said incoming liquid passageway in the liquid conducting member and the passageway in said third longitudinal portion of the tubular element is open at the other end thereof to said outgoing liquid passageway in the liquid conducting member.

10. A medical liquid dispensing device as set forth in claim 9, in which the passageway continuous in said first and second longitudinal portions of the microporous tubular element is closed at said other end thereof by means of an adhesive applied to the tubular element at the leading end of said first longitudinal portion of the tubular element in said incoming liquid passageway in the liquid conducting member.

11. A medical liquid dispensing device as set forth in claim 9, in which said first longitudinal portion of the microporous tubular element is collapsed at its leading end in said incoming liquid passageway in the liquid conducting member so that the passageway continuous in said first and second longitudinal portions of the tubular element is closed at said other end thereof.

12. A medical liquid dispensing device as set forth in claim 11, in which said microporous tubular element further has a fourth longitudinal portion extending from said other of the partition elements into said outgoing liquid passageway in the liquid conducting member and in which said other of the two longitudinal passageways in the microporous tubular element is formed and continuous in the third and fourth longitudinal portions of the tubular element.

13. A medical liquid dispensing device as set forth in claim 12, in which the passageway continuous in said first and second longitudinal portions of the microporous tubular element is closed at the other end thereof in said incoming liquid passageway in the liquid conducting member and the passageway continuous in said third and fourth longitudinal portions of the tubular element is closed at the other end thereof in said outgoing liquid passageway in the liquid conducting member.

14. A medical liquid dispensing device as set forth in claim 13, in which the first and fourth longitudinal portions of said microporous tubular element are collapsed at their respective leading ends in the incoming and outgoing liquid passageways, respectively, in the liquid conducting member so that each of the passageway continuous in said first and second longitudinal portions and the passageway continuous in said third and fourth longitudinal portions of the microporous tubular element is closed at said other end thereof.

15. A medical liquid dispensing device as set forth in claim 13, in which each of the passageway continuous in said first and second longitudinal portions and the passageway continuous in said third and fourth longitudinal portions of said microporous tubular element is closed at said other end thereof by means of an adhesive applied to the tubular element at the leading end of each of the first and fourth longitudinal portions of the tubular element in each of the incoming and outgoing liquid passageways in the liquid conducting member.

16. A medical liquid dispensing device as set forth in claim 1, in which said microporous tubular element has a first longitudinal portion longitudinally extending from one of said partition elements into said intermediate liquid passageway in the liquid conducting member, a second longitudinal portion extending from the other of the partition elements into the intermediate liquid passageway in the liquid conducting member, and a third longitudinal portion extending from said other of said partition elements into said outgoing liquid passageway in the liquid conducting member, wherein one of said two longitudinal passageways in the microporous tubular element is formed in the first longitudinal portion of the tubular element and the other of the two longitudinal passageways in the tubular element is formed and continuous in the second and third longitudinal portions of the tubular element and wherein the microporous tubular element is collapsed between the first and second longitudinal portions thereof so that each of the longitudinal passageways in the tubular element is closed at one end in the intermediate liquid passageway in the liquid conducting member.

17. A medical liquid dispensing device as set forth in claim 16, in which the passageway in said first longitudinal portion of said microporous tubular element is open at the other end thereof to said incoming liquid passageway in the liquid conducting member and the passageway continuous in said second and third longitudinal portions of the tubular element is closed at the other end thereof in said outgoing liquid passageway in the liquid conducting member.

18. A medical liquid dispensing device as set forth in claim 17, in which said third longitudinal portion of the microporous tubular element is collapsed at its leading end in said outgoing liquid passageway in the liquid conducting member so that the passageway continuous in said second and third longitudinal portions of the tubular element is closed at said other end thereof.

19. A medical liquid dispensing device as set forth in claim 17, in which the passageway continuous in said second and third longitudinal portions of the microporous tubular element is closed at said other end thereof by means of an adhesive applied to the tubular element at the leading end of said third longitudinal portion of the tubular element in said outgoing liquid passageway in the liquid conducting member.

20. A medical liquid dispensing device as set forth in claim 1, 2, 3, 4, 5, 6, 7, 8, 9, 11, 10, 16, 17, 18, 19, 12, 13, 14, or 15, in which said microporous tubular element consists of a microporous hollow filament of polyvinyl-alcohol or a rayon fiber.

21. A medical liquid dispensing device as set forth in claim 10, 19 or 15, in which said adhesive is composed of a thermosetting synthetic resin.

* * * * *